(12) United States Patent
Hartwich et al.

(10) Patent No.: US 7,056,664 B1
(45) Date of Patent: Jun. 6, 2006

(54) METHOD OF THE ELECTROCHEMICAL DETECTION OF NUCLEIC ACID OLIGOMER HYBRIDS

(75) Inventors: Gerhard Hartwich, München (DE); Adam Heller, Austin, TX (US)

(73) Assignee: Fritz Biochem Gesellschaft für Bioanalytik mbH, Munich (DE)

( * ) Notice: Subject to any disclaimer, the term of this patent is extended or adjusted under 35 U.S.C. 154(b) by 0 days.

(21) Appl. No.: 09/856,543

(22) PCT Filed: Nov. 19, 1999

(86) PCT No.: PCT/EP99/08888

§ 371 (c)(1),
(2), (4) Date: Dec. 13, 2001

(87) PCT Pub. No.: WO00/31101

PCT Pub. Date: Jun. 2, 2000

(30) Foreign Application Priority Data

Nov. 23, 1998 (DE) ............................... 198 53 957
Apr. 29, 1999 (DE) ............................... 199 21 940

(51) Int. Cl.
*C12Q 1/68* (2006.01)
*C07H 21/00* (2006.01)

(52) U.S. Cl. ......................................... 435/6; 536/23.1
(58) Field of Classification Search .................... 435/6; 536/23.1
See application file for complete search history.

(56) References Cited

U.S. PATENT DOCUMENTS

| | | | | |
|---|---|---|---|---|
| 3,662,745 | A | * | 5/1972 | Cosentino .................... 600/348 |
| 5,102,798 | A | | 4/1992 | Guiseppi-Elie ............. 435/177 |
| 5,312,527 | A | | 5/1994 | Mikkelsen et al. .... 204/153.12 |
| 5,622,946 | A | | 4/1997 | Sessler et al. .............. 514/185 |
| 5,770,369 | A | | 6/1998 | Meade et al. .................. 435/6 |
| 5,824,473 | A | | 10/1998 | Meade et al. .................. 435/6 |
| 5,968,745 | A | * | 10/1999 | Thorp et al. .................. 435/6 |
| 6,060,327 | A | * | 5/2000 | Keen ..................... 204/403.14 |

FOREIGN PATENT DOCUMENTS

| | | |
|---|---|---|
| DE | 42 16 696 A1 | 10/1993 |
| EP | 0 831 327 A1 | 3/1998 |
| WO | 95/15971 | 6/1995 |
| WO | 96/00901 | 1/1996 |
| WO | 96/35940 | 11/1996 |
| WO | 96/40712 | 12/1996 |
| WO | 97/46568 | 12/1997 |
| WO | 98/20162 | 5/1998 |
| WO | 98/31839 | 7/1998 |
| WO | 99/04440 | 1/1999 |
| WO | 99/51778 | 10/1999 |
| WO | 00/31101 | 6/2000 |

OTHER PUBLICATIONS

Wagner et al. "Bioreactive Self-Assembled Monolayers on Hydrogen-Passivated Si (111) as a New Class of Atomatically Flat Substrates for Biological Scanning Probe Microscopy", Journal of Structural Biology 119, pp. 189-201, 1997.*
U.S. Appl. No. 09/056,995, filed Apr. 8, 1998, Barton et al.
Bains, William and Geoff C. Smith. "A Novel Method for Nucleic Aid Sequence Determination", *J. theor. Biol.*, 135, (1988), pp. 303-307.
Catlin, Joseph C., Ronald S. Pardini, G. Doyle Daves, Jr., James C. Heidker and Karl Folkers. "New Hydroxyquinones, Apparent Inhibitors of Coenzyme Q Enzyme Systems", *Journal of the American Chemical Society* 90:13: Jun. 19, 1968, pp. 3572-3574.
*Chemical Abstracts*, vol. 70, 1969, p. 388.
*Chemical Abstracts*, vol. 113, 1990, p. 440.
*Chemical Abstracts*, vol. 115, 1991, p. 30.
*Chemical Abstracts*, vol. 127, 1997, p. 2143.
*Chemical Abstracts*, vol. 129, 1998, pp. 1442-1443.
Daves, Jr., G. Doyle, Joseph J. Wilczynski, Palle Friis and Karl Folkers. "Synthesis of Rhodoquinone and Other Multiprenyl-1, 4-benzoquinones Biosynthetically Related to Ubiquinone", *Journal of the American Chemical Society* 90:20; Sep. 24, 1968, pp. 5587-5593.
Diederichsen, Ulf. "Ladungstransport in DNA: eine Kontroverse", *Angew. Chem.*, 109, Nr. 21, 1997, pp. 2411-2413.
Drmanac, Radoje, Ivan Labat, Ivan Brukner and Radomir Crkvenjakov. "Sequencing of Megabase Plus DNA by Hybridization: Theory of the Method", *Genomics* 4, (1989), pp. 114-128.

(Continued)

Primary Examiner—Jezia Riley
(74) *Attorney, Agent, or Firm*—David & Bujold, P.L.L.C.

(57) ABSTRACT

The invention relates to a method for the electrochemical detection of sequence-specific nucleic acid oligomer hybridization events. To this end single DNA/RNA/PNA oligomer strands which at one end are covalently joined to a support surface and at the other, free end, covalently linked to a redox pair, are used as hybridization matrix (probe). As a result of treatment with the oligonucleotide solution (target) to be examined, the electric communication between the conductive support surface and the redox pair bridged by the single-strand oligonucleotide, which communication initially is either absent or very weak, is modified. In case of hybridization, the electric communication between the support surface and the redox pair, which is now bridged by a hybridized double-strand oligonucleotide, is increased. This permits the detection of a hybridization event by electrochemical methods such as cyclic voltametry, amperometry or conductivity measurement.

6 Claims, 4 Drawing Sheets

OTHER PUBLICATIONS

Eikyu, Yoshiteru, Yoshinori Nakamura, Taishin Akiyama, Fumio Yoneda, Kiyoshi Tanaka and Kaoru Fuji. "Hybridization of Oligodeoxynucleotide with Redox Coenzyme Model; Synthesis and Properties of Thymidine Decamers Covalently Linked to 5-Deazaflavin", *Chem. Pharm. Bull.* 40(1)(1992), pp. 291-293.

Frier, Christelle, Jean-Luc Décout, and Marc Fontecave. "Method for Preparing New Flavin Derivatives: Synthesis of Flavin-Thymine Nucleotides and Flavin-Oligonucleotide Adducts", *J. Org. Chem.* 62, 1997, pp. 3520-3528.

Frier, Christelle, Jean-François Mouscadet, Jean-Luc Décout, Christian Auclair and Marc Fontecave. "Flavin-oligonucleotide conjugates: sequence specific photocleavage of DNA", *Chem. Commun.*, 1998, pp. 2457-2458.

Gasper, Susan M. and Gary B. Schuster. "Intramolecular Photoinduced Electron Transfer to Anthraquinones Linked to Duplex DNA: The Effect of Gaps and Traps on Long-Range Radical Cation Migration", *Journal of the American Chemical Society*, 119, 1997, pp. 12762-12771.

Holmlin, R. Erik, Peter J. Dandliker und Jacqueline K. Barton. "Ladungsübertragung durch den DNA-Basenstapel", *Angew. Chem.*, 109, 1997, pp. 2830-2848.

Holmlin, R. Erik, Ricky T. Tong, and Jacqueline K. Barton. "Long-Range Triplet Energy Transfer Between Metallointercalators Tethered to DNA: Importance of Intercalation, Stacking, and Distance", *Journal of the American Chemical Society*, 120, 1998, pp. 9724-9725.

Hurley, Dennis J. and Yitzhak Tor. "Metal-Containing Oligonucleotides: Solid-Phase Synthesis and Luminescence Properties", *Journal of the American Chemical Society*, 120, 1998, pp. 2194-2195.

Willner, Itamar, Vered Heleg-Shabtai, Ron Blonder, Eugenii Katz, and Guoliang Tao. "Electrical Wiring of Glucose Oxidase by Reconstitution of FAD-Modified Monolayers Assembled onto Au-Electrodes", *Journal of the American Chemical Society*, 118, 1996, pp. 10321-10322.

Willner, Itamar, Eugenii Katz, Bilha Willner, Ron Blonder, Vered Heleg-Shabtai, and Andreas F. Bückmann. "Assembly of Functionalized Monolayers of Redox Proteins on Electrode Surfaces: Novel Bioelectronic and Optobioelectronic Systems", *Biosensors & Bioelectronics*, vol. 12, No. 4, 1997, pp. 337-356.

Ihara, Toshihiro, Masamichi Nakayama, Mitsuru Murata, Koji Nakano and Mizuo Maeda. "Gene Sensor Using Ferrocenyl Oligonucleotide", *Chem. Commun.*, 1997, pp. 1609-1610.

Jacquet, Luc, R. Jeremy H. Davies, Andrée Kirsch-De Mesmaeker, and John M. Kelly. "Photoaddition of Ru(tap)$_2$(bpy)$^{2+}$ to DNA: A New Mode of Covalent Attachment of Metal Complexes to Duplex DNA", *Journal of the American Chemical Society*, 119, 1997, pp. 11763-11768.

Johnston, Dean H., Katherine C. Glasgow and H. Holden Thorp. "Electrochemical Measurement of the Solvent Accessibility of Nucleobases Using Electron Transfer between DNA and Metal Complexes", *Journal of the American Chemical Society*, 117, 1995, pp. 8933-8938.

Katz, Eugenii, Daniela D. Schlereth and Hanns-Ludwig Schmidt. "Electrochemical Study of Pyrroloquinoline Quinone Covalently Immobilized as a Monolayer onto a Cystamine-Modified Gold Electrode", *Journal of Electroanalytical Chemistry*, 367 (1994), pp. 59-70.

Korri-Youssoufi, H., F. Garnier, P. Srivastava, P. Godillot, and A. Yassar. "Toward Bioelectronics: Specific DNA Recognition Based on an Oligonucleotide-Functionalized Polypyrrole", *Journal of the American Chemical Society*, 119, 1997, pp. 7388-7389.

Meggers, Eric, Dirk Kusch, and Bernd Giese. "An Efficient Synthesis of Enantiomerically Pure Δ-Ruthenium(II)-Labelled Oligonucleotides", *Helvetica Chimica Acta*, vol. 80, 1997, pp. 640-652.

Millan, Kelly M., Angela Saraullo, and Susan R. Mikkelsen. "Voltammetric DNA Biosensor for Cyctic Fibrosis Based on a Modified Carbon Paste Electrode", *Analytical Chemistry*, vol. 66, No. 18, Sep. 15, 1994, pp. 2943-2948.

Moore, Harold W. and Karl Folkers. "New Method for Structural Assignments of Hydroxy Analogs of Coenzyme Q$^1$", *Journal of the American Chemistry Society* 88:3, Feb. 5, 1966, pp. 564-570.

Nakamura, Nobuhumi, Takamitsu Kohzuma and Shinnichiro Suzuki. Electrochemical Properties of Coenzyme Pyrroloquinolinequinone Using a Di-(4-pyridyl) Disulfide Modified Gold Electrode under Acidic Conditions:, *The Chemical Society of Japan*, 66 (1993), pp. 1289-1291.

Pasternack, Robert F., Esther J. Gibbs, Peter J. Collings, Julio C. dePaula, L. Christine Turzo, and Antonio Terracina. "A Nonconventional Approach to Supramolecular Formation Dynamics. The Kinetics of Assembly of DNA-Bound Porphyrins", *Journal of the American Chemical Society*, 120, 1998, pp. 5873-5878.

Reed, Michael W., Ansel Wald, and Rich B. Meyer. Triplex-Directed Interstrand DNA Cross-Linking by Diaziridinylquinone-Oligonucleotide Conjugates:, *Journal of the American Chemical Society*, vol. 120, No. 38, Sep. 30, 1998, pp. 9729-9734.

Scott, A. Ian. "How Were Porphyrins and Lipids Synthesized in the RNA World?", *Tetrahedron Letters*, vol. 38, No. 28, 1997, pp. 4961-4964.

Sosnowski, Ronald G., Eugene Tu, William F. Butler, James P. O'Connell, and Michael J. Heller. "Rapid Determination of Single Base Mismatch Mutations in DNA Hybrids by Direct Electric Field Control", *Proc. Natl. Acad. Sci. USA*, vol. 94, Feb. 1997, pp. 1119-1123.

Caruana, Daren J. and Adam Heller, "Enzyme-Amplified Amperometric Detection of Hybridization and of a Single Base Pair Mutation in an 18-Base Oligonucleotide on a 7-μm-Diameter Microelectrode", *J. Am. Chem. Soc.* 1999, vol. 121, No. 4, pp. 769-774.

* cited by examiner

SEQUENCE LISTING

```
<160> NUMBER OF SEQ ID NOS: 2

<210> SEQ ID NO 1
<211> LENGTH: 12
<212> TYPE: PRT
<213> ORGANISM: Artificial Sequence
<220> FEATURE:
<220> FEATURE:
<223> OTHER INFORMATION: Description of Artificial Sequence: artificial
      synthetic oligonucleotides

<400> SEQUENCE: 1

Thr Ala Gly Thr Cys Gly Gly Ala Ala Gly Cys Ala
```

```
<210> SEQ ID NO 2
<211> LENGTH: 12
<212> TYPE: PRT
<213> ORGANISM: Artificial Sequence
<220> FEATURE:
<220> FEATURE:
<223> OTHER INFORMATION: Description of Artificial Sequence: artificial
      synthetic oligonucleotides

<400> SEQUENCE: 2

Ala Thr Cys Ala Gly Ala Thr Thr Thr Cys Gly Thr
 1               5                  10
```

METHOD OF THE ELECTROCHEMICAL DETECTION OF NUCLEIC ACID OLIGOMER HYBRIDS

FIELD OF THE INVENTION

The present invention is directed to a modified nucleic acid oligomer, as well as a method of electrochemically detecting sequence-specific nucleic acid oligomer hybridization events.

BACKGROUND OF THE INVENTION

Generally, gel-electrophoretic methods with autoradiographical or optical detection are used for DNA and RNA sequence analysis, e.g. in disease diagnosis, toxicological test procedures, genetic research and development, as well as in the agrarian and pharmaceutical sectors.

To illustrate the most significant gel-electrophoretic method with optical detection (Sanger method), FIG. 1b shows a DNA fragment with primer. In the Sanger method, a DNA-containing solution is divided into four samples and the primer of each sample is covalently modified with a fluorescent dye that emits at a distinct wavelength. As illustrated in FIG. 1b, deoxyribonucleoside triphosphate of bases A (adenine), T (thymine), C (cytosine), and G (guanine), i.e. dATP, dTTP, dCTP, and dGTP, are added to each sample to enzymatically replicate the single strand, starting at the primer, by means of DNA polymerase 1. In addition to the four deoxyribonucleoside triphosphates, each reaction mixture also contains sufficient 2',3'-dideoxy analog (FIG. 1a) of one of these nucleoside triphosphates as a blocking base (one of each of the four possible blocking bases per sample) to terminate replication at all possible binding sites. After combining the four samples, all lengths of replicated DNA fragments having blocking-base-specific fluorescence result and can be gel-electrophoretically sorted according to length and characterized using fluorescent spectroscopy (FIG. 1c).

Another optical detection method is based on the accumulation of fluorescent dyes such as e.g. ethidium bromide on oligonucleotides. The fluorescence of such dyes increases in comparison with the free solution of the dye by about 20-fold when they accumulate on double-stranded DNA or RNA and can therefore be used to detect hybridized DNA or RNA.

In radiolabeling, $^{32}P$ is built into the phosphate skeleton of the oligonucleotides, with $^{32}P$ usually being added to the 5'-hydroxyl end by means of polynucleotide kinase. Thereafter, the labeled DNA is preferably cleaved, under defined conditions, at one of each of the four nucleotide types, such that an average of one cleavage per chain results. Thus, for a given base type, there are present in the reaction mixture chains extending from the $^{32}P$-label to the position of that base (if there are multiple appearances of the base, chains of varying lengths will result accordingly). The four fragment mixtures are then gel-electrophoretically separated on four lanes. Thereafter, an autoradiogram of the gel is prepared, from which the sequence can be directly read.

Some years ago, a further method of DNA sequencing was developed on the basis of optical (or autoradiographical) detection, namely sequencing by means of oligomer hybridization (cf. e.g. Drmanac et al., Genomics 4, (1989), pp. 114–128 or Bains et al., Theor. Biol. 135, (1988), pp. 303–307). In this method, a complete set of short oligonucleotides, or oligomers (probe oligonucleotides), e.g. all 65,536 possible combinations of the bases A, T, C, and G of an oligonucleotide octamer are bound to a support. The attachment occurs in an ordered grid consisting of 65,536 test sites, with each larger amount of an oligonucleotide combination defining one test site, and the position of each individual test site (oligonucleotide combination) is known. On such a hybridization matrix, the oligomer chip, a DNA fragment whose sequence is to be determined, the target, is labeled with fluorescent dye (or $^{32}P$) and hybridized under conditions that allow only one specific double-strand formation. In this way, the target DNA fragment attaches only to the oligomers (in this example to the octamers) whose complementary sequence corresponds exactly to a portion (an octamer) of its own sequence. Thus, all of the oligomer sequences (octamer sequences) present in the fragment are determined by means of optical (or autoradiographical) detection of the binding position of the hybridized DNA fragment. Due to the overlapping of neighboring oligomer sequences, the continuous sequence of the DNA fragment can be determined using suitable mathematical algorithms. The advantages of this method lie in, among other things, the miniaturization of the sequencing and thus in the enormous amount of data that can be simultaneously captured in one operation. In addition, primer and gel-electrophoretic separation of the DNA fragments can be dispensed with. This principle is demonstrated by example in FIG. 2 for a 13-base-long DNA fragment.

The use of radioactive labels in DNA/RNA sequencing is associated with several disadvantages, such as e.g. elaborate, legally required safety precautions in dealing with radioactive materials, radiation, spatially limited resolution capacity (maximum 1 mm$^2$) and sensitivity that is only high when the radiation of the radioactive fragments act on an X-ray film for an appropriately long time (hours to days). Although the spatial resolution can be increased by means of additional hardware and software, and the detection time can be decreased by means of β-scanners, both of these involve considerable additional costs.

Some of the fluorescent dyes that are commonly used to label the DNA (e.g. ethidium bromide) are mutagenic and require appropriate safety precautions, as does the use of autoradiography. In nearly every case, the use of optical detection requires the use of one or more laser systems, and thus experienced personnel and appropriate safety precautions. The actual detection of the fluorescence requires additional hardware such as e.g. optical components for amplification and, in the case of varying stimulation and query wavelengths as in the Sanger method, a control system. Thus, depending on the stimulation wavelengths required and the detection performance desired, considerable investment costs may result. In sequencing by means of hybridization on the oligomer chip, detection is even more costly because, in addition to the stimulation system, high-resolution CCD cameras (charge coupled device cameras) are needed for 2-dimensionally detecting the fluorescent spots.

Thus, although there are quantitative and extremely sensitive methods for DNA/RNA sequencing, these methods are time consuming, require elaborate sample preparation and expensive equipment, and are generally not available as portable systems.

DESCRIPTION OF THE INVENTION

Therefore, it is the object of the present invention to create for detecting nucleic acid oligomer hybrids an apparatus and a method that do not exhibit the disadvantages of the state of the art.

According to the present invention, this object is solved by the modified oligonucleotide according to independent claim 1, by the method of producing a modified oligonucleotide according to independent claims 9 and 10, by the modified conductive surface according to independent claim 11, the method of producing a modified conductive surface according to independent claim 21, and a method of electrochemically detecting oligomer hybridization events according to independent claim 27.

The following abbreviations and terms are used herein:

| | |
|---|---|
| Genetics | |
| DNA | deoxyribonucleic acid |
| RNA | ribonucleic acid |
| PNA | peptide nucleic acid (Synthetic DNA or RNA in which the sugar-phosphate moiety is replaced by an amino acid. If the sugar-phosphate moiety is replaced by the —NH—$(CH_2)_2$—N(COCH$_2$-base)-CH$_2$CO— moiety, PNA will hybridize with DNA.) |
| A | adenine |
| G | guanine |
| C | cytosine |
| T | thymine |
| base | A, G, T, or C |
| bp | base pair |
| nucleic acid | At least two covalently joined nucleotides or at least two covalently joined pyrimidine (e.g. cytosine, thymine, or uracil) or purine bases (e.g. adenine or guanine). The term nucleic acid refers to any backbone of the covalently joined pyrimidine or purine bases, such as e.g. to the sugar-phosphate backbone of DNA, cDNA, or RNA, to a peptide backbone of PNA, or to analogous structures (e.g. a phosphoramide, thiophosphate, or dithiophosphate backbone). The essential feature of a nucleic acid according to the present invention is that it can sequence-specifically bind naturally occurring cDNA or RNA. |
| nucleic acid oligomer | Nucleic acid of base length that is not further specified (e.g. nucleic acid octamer: a nucleic acid having any backbone in which 8 pyrimidine or purin bases are covalently bound to one another). |
| oligomer | Equivalent to nucleic acid oligomer. |
| oligo-nucleotide | Equivalent to oligomer or nucleic acid oligomer, thus e.g. a DNA, PNA, or RNA fragment of base length that is not further specified. |
| oligo | Abbreviation for oligonucleotide. |
| dATP | Deoxyribonucleoside triphosphate of A (DNA moiety with the A base and two further phosphates to build a longer DNA fragment or oligonucleotide). |
| dGTP | Deoxyribonucleoside triphosphate of G (DNA moiety with the G base and two further phosphates to build a longer DNA fragment or oligonucleotide). |
| dCTP | Deoxyribonucleoside triphosphate of C (DNA moiety with the C base and two further phosphates to build a longer DNA fragment or oligonucleotide). |
| dTTP | Deoxyribonucleoside triphosphate of T (DNA moiety with the T base and two further phosphates to build a longer DNA fragment or oligonucleotide). |
| primer | Initial complementary fragment of an oligonucleotide, with the base length of the primer being only approx. 4–8 bases. Serves as the starting point for enzymatic replication of an oligonucleotide. |
| mismatch | To form the Watson Crick double-stranded oligonucleotide structure, the two single strands hybridize in such a way that the A (or C) base of one strand forms hydrogen bonds with the T (or G) base of the other strand (in RNA, T is replaced by uracil). Any other base pairing does not form hydrogen bonds, distorts the structure, and is referred to as a "mismatch." |
| ds | double strand |
| ss | single strand |
| Chemical Substances/Groups | |
| R | A substituent or side chain of any organic residue not further specified. |
| redox | redox-active substance |
| alkyl | The term "alkyl" refers to a saturated hydrocarbon radical that is straight-chained or branched (e.g. ethyl, isopropyl, or 2,5-dimethylhexyl, etc.). When "alkyl" is used to indicate a linker or spacer, the term refers to a group having two available valences for covalent linkage (e.g. —CH$_2$CH$_2$—, —CH$_2$CH$_2$CH$_2$—, or —CH$_2$C(CH$_3$)$_2$CH$_2$CH$_2$C(CH$_3$)$_2$CH$_2$—, etc.). Alkyl groups preferred as substituents or side chains R are those of chain length 1–30 (longest continuous chain of atoms bound to one another). Alkyl groups preferred as linkers or spacers are those of chain length 1–20, especially of chain length of 1–14, the chain length representing the shortest continuous link between linker or spacer-joined structures. |
| alkenyl | Alkyl groups in which one or more of the C—C single bonds are replaced by C=C double bonds. |
| alkinyl | Alkyl or alkenyl groups in which one or more of the C—C single or C=C double bonds are replaced by C≡C triple bonds. |
| heteroalkyl | Alkyl groups in which one or more of the C—H bonds or C—C single bonds are replaced by C—N, C=N, C—P, C=P, C—O, C=O, C—S, or C=S bonds. |
| hetero-alkenyl | Alkenyl groups in which one or more C—H bonds, C—C single, or C=C double bonds are replaced by C—N, C=N, C—P, C=P, C—O, C=O, C—S, or C=S bonds. |
| heteroalkinyl | Alkinyl groups in which one or more of the C—H bonds, C—C single, C=C double, or C≡C triple bonds are replaced by C—N, C=N, C—P, C=P, C—O, C=O, C—S, or C=S bonds. |
| linker | A molecular link between two molecules or between a surface atom, surface molecule, or surface molecule group and another molecule. Linkers can usually be purchased in the form of alkyl, alkenyl, alkinyl, heteroalkyl, heteroalkenyl, or heteroalkinyl chains, the chain being derivatized in two places with (identical or different) reactive groups. These groups form a covalent chemical bond in simple/known chemical reactions with the appropriate reaction partner. The reactive groups may also be photoactivatable, i.e. the reactive groups are activated only by light of a specific or random wavelength. Preferred linkers are those of chain length of 1–20, especially of chain length of 1–14, the chain length representing here the shortest continuous link between the structures to be joined, thus between the two molecules or between a surface atom, surface molecule, or surface molecule group and another molecule. |
| spacer | A linker that is covalently attached via the reactive groups to one or both of the structures to be joined (see linker). Preferred spacers are those of chain length 1–20, especially of chain length 1–14, the chain length representing the shortest continuous link between the structures to be joined. |
| (n × HS-spacer)-oligo | A nucleic acid oligomer to which n thiol functions are each attached via a spacer, where each spacer may have a different chain length (shortest continuous link between the thiol function and the nucleic acid oligomer), especially any chain length between 1 and 14 each. These spacers, in turn, may be bound to various reactive groups that are naturally present on the nucleic acid oligomer or that have been fixed thereto by means of modification, and "n" is any integer, especially a number between 1 and 20. |
| (n × R-S-S-spacer)-oligo | A nucleic acid oligomer to which n disulfide functions are each attached via a spacer, and any residue R saturates the disulfide function. Each spacer for attaching the disulfide function to the nucleic acid oligomer may have a different chain length (shortest continuous link between the disulfide function and the nucleic acid oligomer), especially any chain length between 1 and 14 each. These spacers, in turn, may be bound to various reactive groups that are naturally present on the nucleic acid oligomer or that have been fixed thereto by means of modification. The placeholder "n" is any integer, especially a number between 1 and 20. |
| oligo-spacer-S-S-spacer-oligo | Two identical or different nucleic acid oligomers that are joined to each other via a disulfide bridge, the disulfide bridge being attached to the nucleic acid oligomers via any two spacers and the two spacers potentially having differing chain lengths (shortest continuous link between the disulfide bridge and the respective nucleic acid oligomer), especially any chain length between 1 and 14 each, and these spacers, in turn, potentially being bound to various |

-continued

| | |
|---|---|
| | reactive groups that are naturally present on the nucleic acid oligomer or that have been fixed thereto by means of modification. |
| PQQ | pyrroloquinoline quinone; corresponds to 4,5-dihydro-4,5-dioxo-1H-pyrrolo-[2,3-f]-quinoline-2,7,9-tricarboxylic acid) |
| TEATFB | tetraethylammonium-tetrafluoroborate |
| sulfo-NHS | N-hydroxysulfosuccinimide |
| EDC | (3-dimethylaminopropyl)-carbodiimide |
| HEPES | N-[2-hydroxyethyl]piperazine-N'-[2-ethanesulfonic acid] |
| Tris | trishydroxymethylamino methane |
| EDTA | ethylenediamine tetraacetate (sodium salt) |
| cystamine | $(H_2N-CH_2-CH_2-S-)_2$ |
| Modified Surfaces/Electrodes | |
| mica | Muskovite platelets, a support for the application of thin layers. |
| Au-S-ss-oligo-PQQ | Gold film on mica having a covalently applied monolayer of derivatized 12-bp single-strand oligonucleotide (sequence: TAGTCGGAAGCA) SEQ ID NO: 1. Here, the terminal phosphate group of the oligonucleotide at the 3' end is esterified with $(HO-(CH_2)_2-S)_2$ to $P-O-(CH_2)_2-S-S-(CH_2)_2-OH$, homolytically cleaving the S—S bond and producing one Au-S-R bond each. The terminal thymine base at the 5' end of the oligonucleotide is modified at the C-5 carbon with $-CH=CH-CO-NH-CH_2-CH_2-NH_2$ and the residue, in turn, is joined via its free amino group with a carboxylic-acid group of the PQQ by means of amidation. |
| Au-S-ds-oligo-PQQ | Au-S-ss-oligo-PQQ that is hybridized with the oligonucleotide complementary to the ss-oligo (sequence: TAGTCGGAAGCA SEQ ID NO: 1). |
| Electrochemistry | |
| E | The electrode potential on the working electrode. |
| $E_0$ | Half-wave potential, the potential in the middle between the current maximums for oxidation and reduction of cyclic voltammetrically reversible electrooxidation or reduction. |
| i | current density (current per cm$^2$ of electrode surface) |
| cyclic voltammetry | Recording a current-voltage curve. The potential of a stationary working electrode is changed linearly as a function of time, starting at a potential at which no electrooxidation or reduction occurs, up to a potential at which a species that is solute or adsorbed on the electrode is oxidized or reduced (i.e. current flows). After running through the oxidation or reduction operation, which produces in the current-voltage curve an initially increasing current and, after reaching a maximum, a gradually decreasing current, the direction of the potential feed is reversed. The behavior of the products of electrooxidation or electroreduction is then recorded in reverse run. |
| amperometry | Recording a current-time curve. Here, the potential of a stationary working electrode is set, e.g. by means of a potential jump, to a potential at which the electrooxidation or reduction of a solute or adsorbed species occurs, and the flowing current is recorded as a function of time. |

The present invention is directed to a nucleic acid oligomer that is modified by the chemical attachment of a redox-active substance. According to the present invention, the nucleic acid oligomer is a compound consisting of at least two covalently joined nucleotides or at least two covalently joined pyrimidine (e.g. cytosine, thymine, or uracil) or purine bases (e.g. adenine or guanine), preferably a DNA, RNA, or PNA fragment. As used herein, the term nucleic acid refers to any backbone of the covalently joined pyrimidine or purine bases, such as e.g. to the sugar-phosphate backbone of DNA, cDNA, or RNA, to a peptide backbone of PNA, or to analogous backbone structures such as e.g. a thiophosphate, a dithiophosphate, or a phosphoramide backbone. The essential feature of a nucleic acid according to the present invention is that it can sequence-specifically bind naturally occurring cDNA or RNA. The terms "(probe) oligonucleotide," "nucleic acid," and "oligomer" are used as alternatives to the term "nucleic acid oligomer."

The redox-active substance is selectively oxidizable and reducible at a potential φ, where φ satisfies the condition 2.0 V≧φ≧–2.0 V. The potential refers here to the free, unmodified, redox-active substance in a suitable solvent, measured against normal hydrogen electrode. According to the present invention, the potential range 1.7 V≧φ≧–1.7 V is preferred, the range 1.4 V≧φ≧–1.2 V being particularly preferred, and the range 0.9 V≧φ≧–0.7 V, in which the redox-active substances of the application example are reduced and reoxidized, being most particularly preferred. In addition, the present invention is directed to a conductive surface to which a nucleic acid oligomer having an attached redox-active substance is chemically bound, directly or indirectly (via a spacer). Furthermore, the present invention is directed to a method of producing a modified conductive surface, wherein a modified nucleic acid oligomer is applied to a conductive surface. According to a further aspect, the present invention is directed to a method that allows electrochemical detection of molecular structures, especially electrochemical detection of DNA/RNA/PNA fragments in a probe solution by means of sequence-specific nucleic acid oligomer hybridization. Detection of hybridization events by means of electrical signals is a simple and economical method and, in a battery-operated variation of a sequencing device, allows on-site application.

Binding a Redoxactive Moiety to a Nucleic Acid Oligomer

For the method of the present invention, it is necessary to bind a redox-active substance to a nucleic acid oligomer. According to the present invention, any redox-active substance may be used for this purpose as long as it is selectively oxidizable and reducible at a potential φ that satisfies the condition 2.0 V≧φ≧–2.0 V. The potential refers here to the free, unmodified, redox-active substance in a suitable solvent, measured against normal hydrogen electrode. According to the present invention, the potential range 1.7 V≧φ≧–1.7 V is preferred, the range 1.4 V≧φ≧–1.2 V is particularly preferred, and the range 0.9 V≧φ≧–0.7 V, in which the redox-active substances of the application example are reduced and reoxidized, is most particularly preferred. According to the present invention, the term "selectively oxidizable and reducible" is understood to mean a redox reaction, i.e. giving up or taking in an electron, that occurs selectively at the location of the redox-active substance. Thus, in the end, no other part of the nucleic acid oligomer is reduced or oxidized by the potential applied, but rather, exclusively the redox-active substance bound to the nucleic acid oligomer.

According to the present invention, a redox-active substance is understood to mean any molecule that, in the electrochemically accessible potential range of the respective support surface (electrode), can be electrooxidized/electroreduced by applying an external voltage to that electrode. In additon to common organic and anorganic redox-active substances such as e.g. hexacyanoferrates, ferrocenes, acridines, or phtalocyanines, redox-active dyes such as e.g. (metallo-) porphyrins of the general Formula 1, (metallo-) chlorophylls of the general Formula 2, or (metallo-) bacteriochlorophylls of the general Formula 3, (colored) naturally occurring oxidation agents such as e.g. flavines of the general Formula 4, pyridine-nucleotides of the general Formula 5 or pyrrolo-quinoline quinones (PQQ) of the general Formula 6, or other quinones such as e.g. 1,4-benzoquinones of the general Formula 7, 1,2-benzoquinones of the general Formula 8, 1,4-naphthoquinones of the general Formula 9, 1,2-naphthoquinones of the general Formula 10, or 9,10-anthraquinones of the general Formula 11 are particularly suitable for attachment to the probe oligonucleotide.

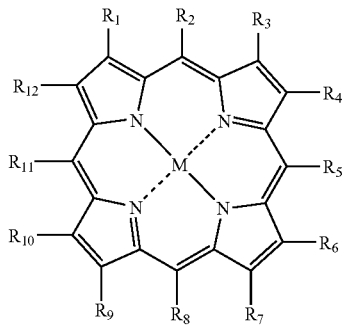
Formula 1

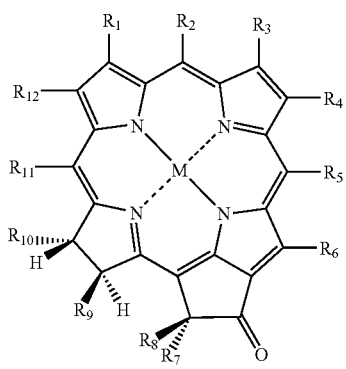
Formula 2

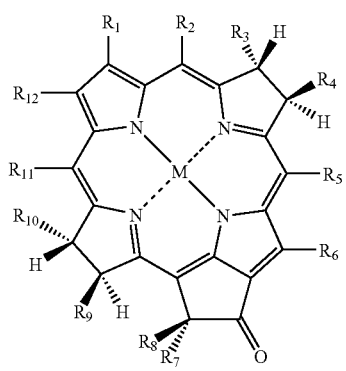
Formula 3

M=2H, Mg, Zn, Cu, Ni, Pd, Co, Cd, Mn, Fe, Sn, Pt, etc.;
$R_1$ to $R_{12}$ are, independently of one another, H or any alkyl, alkenyl, alkinyl, heteroalkyl, heteroalkenyl, or heteroalkinyl substituents.

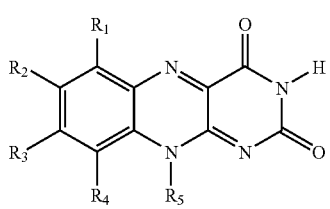
Formula 4

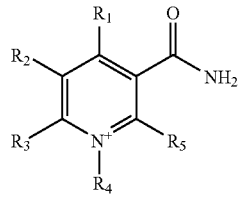
Formula 5

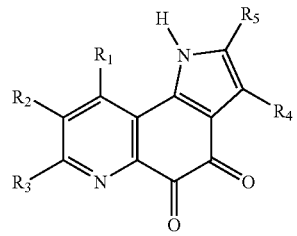
Formula 6

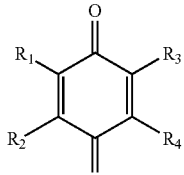
Formula 7

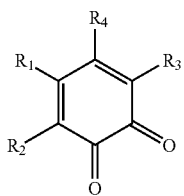
Formula 8

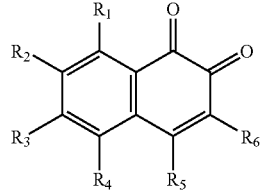
Formula 9

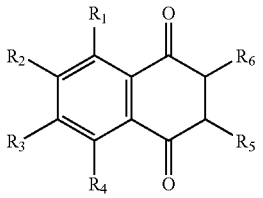
Formula 10

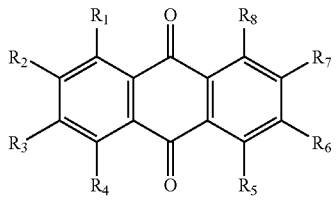
Formula 11

$R_1$ to $R_8$ are, independently of one another, H or any alkyl, alkenyl, alkinyl, heteroalkyl, heteroalkenyl, or heteroalkinyl substituents.

According to the present invention, a redox-active substance is covalently bound to an oligonucleotide by means of the oligonucleotide reacting with the redox-active substance. This bond can be achieved in three different ways:

a) The reactive group for forming a bond at the nucleic acid oligomer is a free phosphoric-acid, sugar-C-3-hydroxy, carboxylic-acid, or amine group of the oligonucleotide backbone, especially a group at one of the two ends of the oligonucleotide backbone. The free, terminal phosphoric-acid, sugar-C-3-hydroxy, carboxylic-acid, or amine groups exhibit increased reactivity and thus easily undergo typical reactions such as e.g. amidation with (primary or secondary) amino groups or with acid groups, esterification with (primary, secondary, or tertiary) alcohols or with acid groups, thioester formation with (primary, secondary, or tertiary) thioalcohols or with acid groups, or condensation of amine and aldehyde with subsequent reduction of the resultant CH=N bond to a $CH_2$—NH bond. The coupling group required for the covalent attachment of the redox-active substance (acid, amine, alcohol, thioalcohol, or aldehyde function) is either naturally present on the redox-active substance or is obtained by means of chemical modification of the redox-active substance.

b) The nucleic acid oligomer is modified with a reactive group at the oligonucleotide backbone or at a base via a covalently attached molecular moiety (spacer) of any composition and chain length (representing the shortest continuous link between the structures to be joined), especially of chain length 1 to 14. The modification preferably occurs at one of the ends of the oligonucleotide backbone or at a terminal base. Spacers may be e.g. an alkyl, alkenyl, alkinyl, heteroalkyl, heteroalkenyl, or heteroalkinyl substituent. Possible simple reactions for forming the covalent bond between the redox-active substance and the nucleic acid oligomer so modified are, as described under a), amidation from an acid and amino group, esterification from an acid and alcohol group, thioester formation from an acid and thioalcohol group, or condensation of aldehyde and amine with subsequent reduction of the resultant CH=N bond to a $CH_2$—NH bond.

According to a preferred embodiment, the nucleic acid oligomer is modified using a redox-active substance that exhibits regions having a predominantly planar p-π-orbital system extended in a plane, such as e.g. the PQQ of Example 1 or the quinones of Formulas 5 or 7–12 or the porphinoid structures of Formulas 1–4 or the pyridine nucleotides of the general Formula 6, or derivatives of these redox-active substances. In this case, the spacer via which the redox-active substance is bound to the nucleic acid oligomer can be selected in such a way that the plane of the p-π-orbitals of the redox-active substance can arrange itself parallel to the p-π-orbitals of the nucleic acid oligomer bases that border on the redox-active substance. This spatial arrangement of the redox-active substance with partially planar p-π-orbitals extended in a plane proves to be particularly favorable.

c) In synthesizing the nucleic acid oligomer, a terminal base will be replaced by the redox-active substance.

According to the present invention, binding the redox-active substance to the oligonucleotide as described under a) and b) may occur before or after binding the oligonucleotide to the conductive surface. The attachment of the redox-active substance to the oligonucleotide bound to the conductive surface then likewise occurs as described under a) and b).

If there are several different oligonucleotide combinations (test sites) on a common surface, it is advantageous to standardize the (covalent) attachment of the redox-active substance to the probe oligonucleotides for the entire surface by the appropriate choice of reactive group at the free probe oligonucleotide ends of the various test sites.

The Conductive Surface

According to the present invention, the term "conductive surface" refers to any support having an electrically conductive surface of any thickness, especially surfaces made of platinum, palladium, gold, cadmium, mercury, nickel, zinc, carbon, silver, copper, iron, lead, aluminum, and manganese. According to the present invention, the terms "electrode" and "conductive (support) surface" are used as alternatives to "conductive surface."

In addition, any doped or non-doped semiconductor surfaces of any thickness may also be used. All semiconductors are useful in the form of pure substances or as mixtures. Examples include, but are not limited to, carbon, silicon, germanium, α tin, and Cu(I) and Ag(I) halides of any crystal structure. Likewise suitable are all binary compounds of any composition and any structure of the elements of groups 14 and 16, of the elements of groups 13 and 15, and of the elements of groups 15 and 16. In addition, ternary compounds of any composition and any structure of the elements of groups 11, 13, and 16 or of the elements of groups 12, 13, and 16 may be used. The designations of the groups of the periodic system refer to the IUPAC recommendation of 1985.

Binding an Oligonucleotide to the Conductive Surface

According to the present invention, a nucleotide is linked directly or via a linker/spacer with the support surface atoms or molecules of a conductive support surface of the kind described above. This bond may be carried out in three different ways:

a) The surface is modified in such a way that a reactive molecule group is accessible. This may occur by means of direct derivatization of the surface molecules, e.g. by means of wet chemical or electrochemical oxidation/reduction. Thus e.g. the surface of graphite electrodes can be wet-chemically supplied with aldehyde or carboxylic-acid groups by means of oxidation. Electrochemically, it is possible e.g. by means of reduction in the presence of aryl-diazonium salts to couple the corresponding (functionalized, i.e. supplied with a reactive group) aryl radical, or by means of oxidation in the presence of $R'CO_2H$ to couple the (functionalized) R' radical to the graphite electrode surface. An example of direct modification of semiconductor surfaces is the derivatization of silicon surfaces to reactive silanols, i.e. silicon supports having Si—OR" groups on the surface, where both R" and R' are any functionalized organic residue (e.g. alkyl, alkenyl, alkinyl, heteroalkyl, heteroalkenyl, or heteroalkinyl substituent). Alternatively, the entire surface may be modified by covalently attaching a reactive group of a bifunctional linker such that a monomolecular layer consisting of any molecules and containing a reactive group, preferably terminally, results on the surface. The term "bifunctional linker" is understood to mean any molecule of any chain length, especially of chain lengths 2-14, having two identical (homobifunctional) or two different (heterobifunctional) reactive molecule groups.

If several different test sites are to be formed on the surface by making use of the methodology of photolithography, then at least one of the reactive groups of the homobifunctional or heterobifunctional linkers is a photoinducible reactive group, i.e. a group that becomes reactive only upon irradiation with light of a specific or random wavelength. This linker is applied in such a way that the/a photoactivatable reactive group is available after the linker is covalently attached to the surface. The nucleic acid oligomers are covalently attached to the surface so modified and are, themselves, modified with a reactive group, preferably near an end of the nucleic acid oligomer, via a spacer of any composition and chain length, especially of chain length 1–14. The reactive group of the oligonucleotide is a group that reacts directly (or indirectly) with the modified surface to form a covalent bond. In addition, a further reactive group may be bound to the nucleic acid oligomers near its second end, this reactive group, in turn, being attached, as described above, directly or via a spacer of any composition and chain length, especially of chain length 1–14. Furthermore, as an alternative to this further reactive group, the redox-active substance may be attached at this second end of the nucleic acid oligomer.

b) The nucleic acid oligomer to be applied to the conductive surface is modified with one or more reactive groups via a covalently attached spacer of any composition and chain length, especially of chain length 1–14, these reactive groups being located preferably near an end of the nucleic acid oligomer. The reactive groups are groups that can react directly with the unmodified surface. Some examples are: (i) thiol-(HS) or disulfide-(S—S—) derivatized nucleic acid oligomer of the general formula (n×HS-spacer)-oligo, (n×R—S—S-spacer)-oligo, or oligo-spacer-S—S-spacer-oligo that react with a gold surface to form gold-sulfur bonds, or (ii) amines that accumulate on platinum or silicon sufaces by means of chemisorption or physisorption. In addition, a further reactive group may be bound to the nucleic acid oligomers near its second end, this reactive group, in turn, being attached, as described above, directly or via a spacer of any composition and chain length, especially of chain length 1–14. Furthermore, as an alternative to this further reactive group, the redox-active substance may be attached at this second end of the oligonucleotide. Particularly nucleic acid oligomers that are modified with several spacer-bridged thiol or disulfide bridges ((n× HS-spacer)-oligo or (n×R—S—S-spacer)-oligo) have the advantage that such nucleic acid oligomers can be applied to the conductive surface at a particular setting angle (angle between the surface normal and the helix axis of a double-stranded helical nucleic acid oligomer or between the surface normal and the axis perpendicular to the base pairs of a double-stranded non-helical nucleic acid oligomer) if the spacers attaching the thiol or disulfide functions to the nucleic acid oligomer possess an increasing or decreasing chain length as viewed from an end of the nucleic acid.

c) Phosphoric-acid, sugar-C-3-hydroxy, carboxylic-acid, or amine groups of the oligonucleotide backbone, especially terminal groups, are used as the reactive group on the probe nucleic acid oligomer. The phosphoric-acid, sugar-C-3-hydroxy, carboxylic-acid, or amine groups exhibit greater reactivity and thus easily undergo typical reactions such as amidation with (primary or secondary) amino or acid groups, esterification with (primary, secondary, or tertiary) alcohols or acid groups, thioester formation with (primary, secondary, or tertiary) thioalcohols or acid groups, or condensation of amine and aldehyde with subsequent reduction of the resultant CH=N bond to a $CH_2$—NH bond. In this case, the coupling group required for the covalent attachment to the phosphoric-acid, sugar-C-3-hydroxy, carboxylic-acid, or amine group is part of the surface derivatization with a (monomolecular) layer of any molecule length, as described under a) in this section, or the phosphoric-acid, sugar-C-3-hydroxy, carboxylic-acid, or amine group can react directly with the unmodified surface, as described under b) in this section. In addition, a further reactive group may be bound to the oligonucleotides near its second end, this reactive group, in turn, being attached, as described above, directly or via a spacer of any composition and chain length, especially of chain length 1–14. Furthermore, as an alternative to this further reactive group, the redox-active substance may be attached at this second end of the nucleic acid oligomer.

Alternatively, binding the oligonucleotide to the conductive surface may occur before or after attaching the redox-active substance to the oligonucleotide, or before or after attaching the spacer supplied with a reactive group for binding the redox-active substance. Binding the already modified oligonucleotide to the conductive surface, i.e. binding to the surface after attaching the redox-active substance to the oligonucleotide, or after attaching the spacer supplied with a reactive group for binding the redox-active substance, likewise takes place as described under a) to c) (in the section "Binding an Oligonucleotide to the Conductive Surface").

In producing the test sites, care must be taken when attaching the single-strand oligonucleotides to the surface that a sufficiently large distance remains between the individual oligonucleotides to provide the necessary space for a hybridization with the target oligonucleotide. To this end, two different methods of proceeding, among others, present themselves:

1.) Producing a modified support surface by attaching a hybridized oligonucleotide, i.e. a support surface derivatization with hybridized probe oligonucleotide instead of with single-strand probe oligonucleotide. The oligonucleotide strand used for hybridization is unmodified (the surface attachment is carried out as described under a)–c) in the section "Binding an Oligonucleotide to the Conductive Surface"). Thereafter, the hybridized oligonucleotide double strand is thermally dehybridized, thus producing a single-strand-oligonucleotide-modified support surface having greater distance between the probe oligonucleotides.

2.) Producing a modified support surface by attaching a single-strand or double-strand oligonucleotide, and adding during support surface derivatization a suitable monofunctional linker that, in addition to the single-strand or double-strand oligonucleotide, is also bound to the surface (the surface attachment is carried out as described under a)–c) in the section "Binding an Oligonucleotide to the Conductive Surface"). According to the present invention, the monofunctional linker has a chain length that is identical to the chain length of the spacer between the support surface and the oligonucleotide, or that differs by a maximum of eight chain atoms. If double-strand oligonucleotide is used for support-surface derivatization, the hybridized oligonucleotide double strand is thermally dehybridized after attaching the double-strand oligonucleotide and the linker to the support surface, as described under 1.) above. By simultaneously attaching a linker to the surface, the distance between the single-strand or double-strand nucleic acid oligomers that are likewise bound to the surface is increased. If a double-strand nucleic acid oligomer is used, this effect is amplified further by the subsequent thermal dehybridization.

Method of Electrochemically Detecting Nucleic Acid Oligomer Hybrids

Advantageously, according to the method of electrochemical detection, several probe oligonucleotides varying in sequence, ideally all necessary combinations of the nucleic acid oligomer, are applied to an oligomer chip or DNA chip to reliably detect the sequence of any target oligomer or of a (fragmented) target DNA, or to seek and sequence-specifically detect mutations in the target. To this end, the support surface atoms or molecules of a defined area (a test site) are linked with DNA/RNA/PNA oligonucleotides of known but random sequence on a conductive support surface, as described above. In a most general embodiment, however, the DNA chip may also be derivated with a single probe oligonucleotide. Preferred probe oligonucleotides are nucleic acid oligomers (DNA, RNA, or PNA fragments) of base length 3 to 50, preferably of length 5 to 30, particularly preferably of length of 7 to 25. According to the present invention, a redox-active substance is bound to the probe oligonucleotides either before or after the latter is bound to the conductive surface.

If the modification of the probe oligonucleotides occurs before the bond to the conductive surface, then the already modifed probe oligonucleotides are bound to the conductive surface as described above. Alternatively, the non-modified probe oligonucleotides bound to the conductive surface are modified with a redox-active substance at the second, free end of the oligonucleotide chain, directly or indirectly via a spacer.

In both cases, a surface hybrid of the general structure elec-spacer-ss-oligo-spacer-redox (FIG. 3) results. The electrical communication between the (conductive) support surface and the redox-active substance ("redox") bridged via a single-strand oligonucleotide in the general structure elec-spacer-ss-oligo-spacer-redox is weak or not present at all. The bridges may, of course, also be carried out without spacers or with only one spacer (elec-ss-oligo-spacer-redox or elec-spacer-ss-oligo-redox). In a next step, the test sites are brought into contact with the oligonucleotide solution (target) to be examined. Hybridization will only occur if the solution contains oligonucleotide strands that are complementary to the probe oligonucleotides bound to the conductive surface, or at least widely complementary. In the case of hybridization between the probe and target oligonucleotide, there will be increased conductivity between the support surface and the redox-active substance because these are now bridged via the oligonucleotide composed of a double strand (shown schematically in FIG. 3 using an example of the elec-spacer-ss-oligo-spacer-redox).

Because of the change in the electrical communication between the (conductive) support surface and the redox-active substance due to the hybridization of the probe oligonucleotide and the oligonucleotide strand (target) complementary to it, a sequence-specific hybridization event can thus be detected using electrochemical methods such as e.g. cyclic voltammetry, amperometry, or conductivity measurements.

In a particularly preferred embodiment of the present invention, a redox-active substance is used that exhibits regions having a predominantly planar p-π-orbital system extended in a plane, such as e.g. the PQQ of Example 1 (cf. FIG. 3), or the quinones of Formula 5 or 7–12 or the porphinoid structures of Formulas 1–4, the pyridine nucleotides of the general Formula 6 and derivatives of these redox-active substances. In this case, the spacer between the nucleic acid oligomer and the redox-active substance is selected in such a way that the plane of the p-π-orbitals of the redox-active substance can arrange itself parallel to the p-π-orbitals of the base pair of the nucleic acid oligomer hybridized with the complimentary strand and bordering on the redox-active substance. This spatial arrangement of the redox-active substance with partially planar p-7α-orbitals extended in a plane proves to be particularly favorable for the electrical conductivity of the double-strand nucleic acid oligomers.

In cyclic voltammetry, the potential of a stationary working electrode is changed linearly as a function of time. Starting at a potential at which no electrooxidation or reduction occurs, the potential is changed until the redox-active substance is oxidized or reduced (i.e. current flows). After running through the oxidation or reduction operation, which produces in the current-voltage curve an initially increasing current, a maximum current (peak), and then a gradually decreasing current, the direction of the potential feed is reversed. The behavior of the products of electrooxidation or electroreduction is then recorded in reverse run.

An alternative electrical detection method, amperometry, is made possible by the fact that the redox-active substance is electrooxidized (electroreduced) by applying a suitable, constant electrode potential, but rereducing (reoxidizing) the redox-active substance to its original state is achieved, not by changing the electrode potential as in cyclic voltammetry, but rather by means of a suitable reducing agent (oxidizing agent) added to the target solution, closing the current circuit of the entire system. As long as reducing agent (oxidizing agent) is present, or as long as the consumed reducing agent (oxidizing agent) is rereduced (reoxidized) on the counter electrode, current flows that can be amperometrically detected and that is proportional to the number of hybridization events.

BRIEF DESCRIPTION OF THE DRAWINGS

The invention will be explained in greater detail using the following application example and the accompanying drawings.

CARRYING OUT THE INVENTION

Figure 1A:
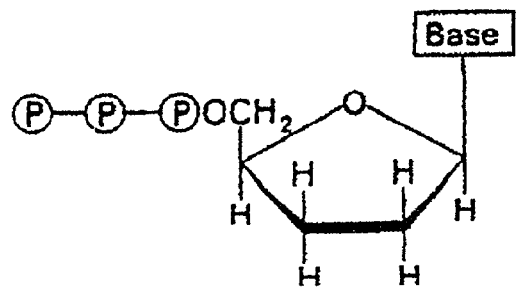
FIG. 1  Shows a schematic illustration of the Sanger method of oligonucleotide sequencing.
Figure 1B:
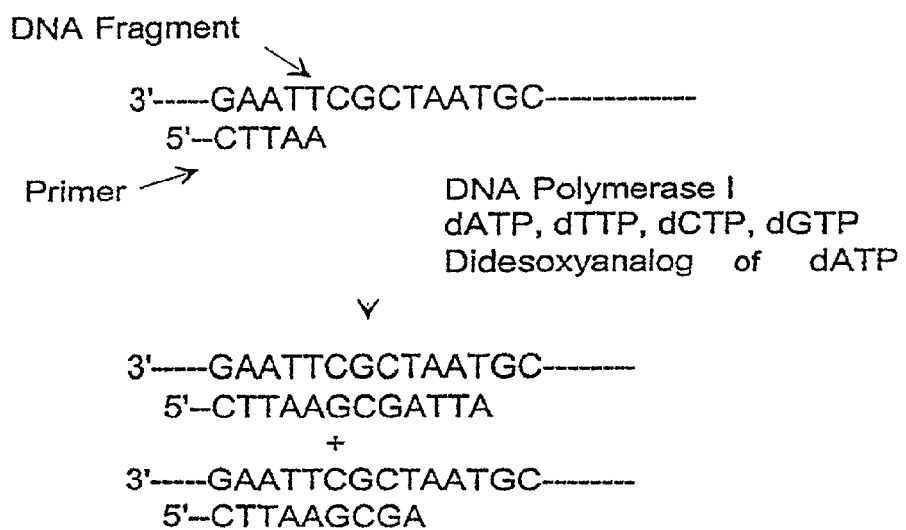
Figure 1C:
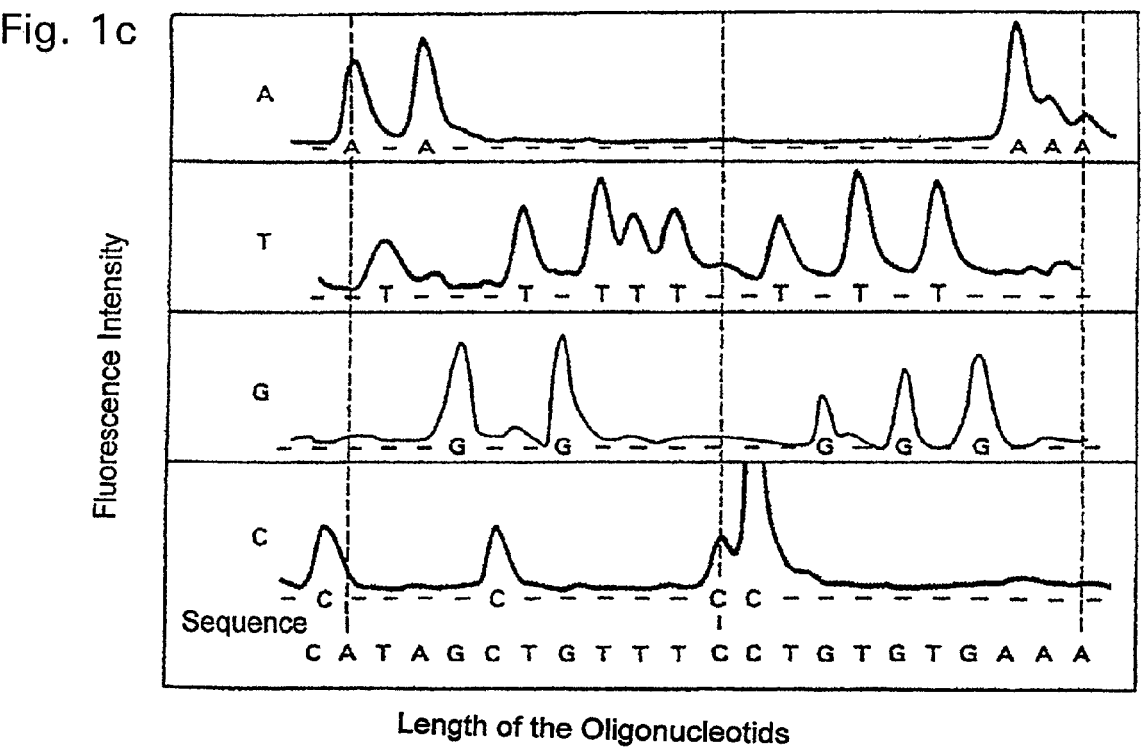
Figure 2:
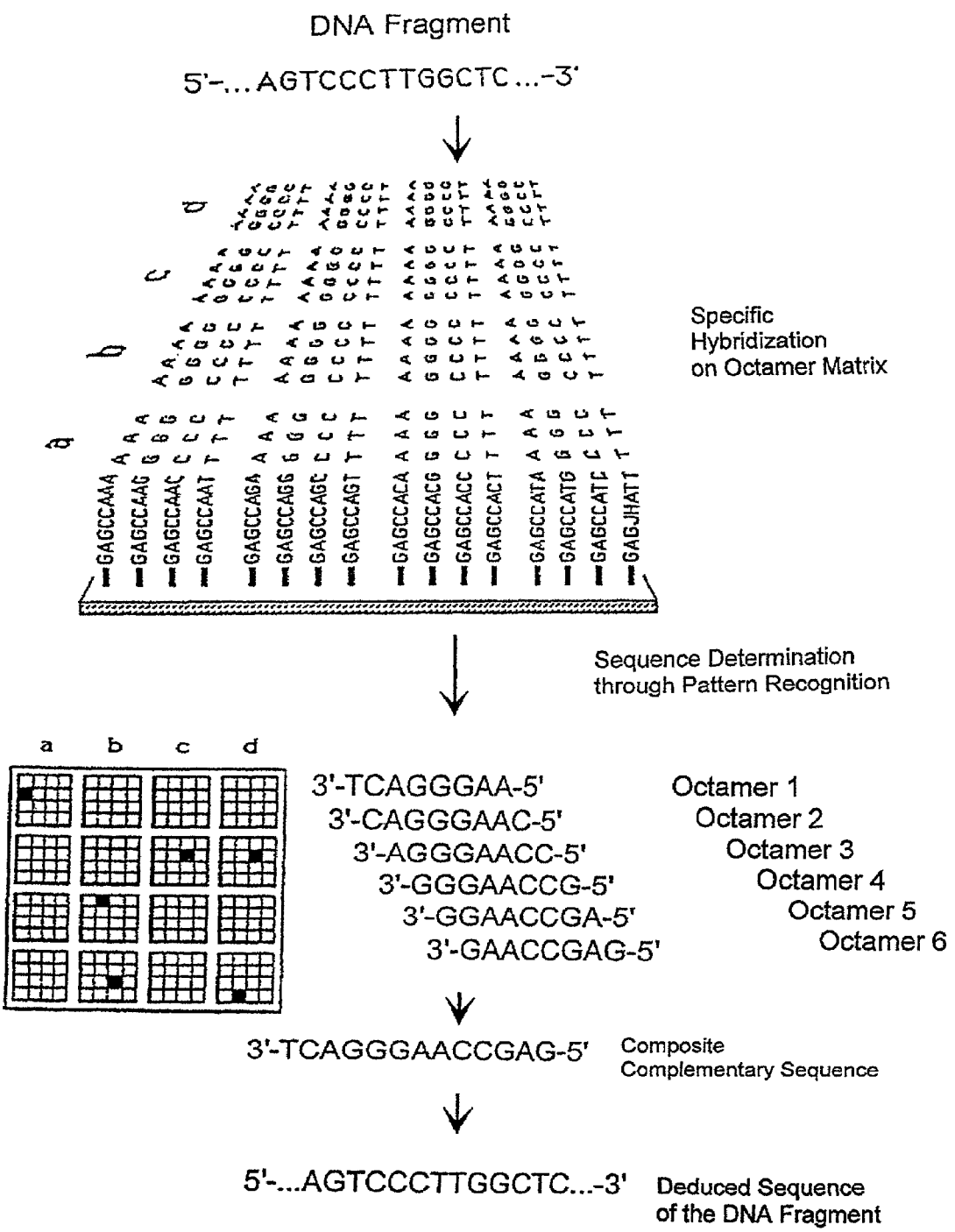
FIG. 2  Shows a schematic illustration of oligonucleotide sequencing by means of hybridization on a chip.
Figure 3:
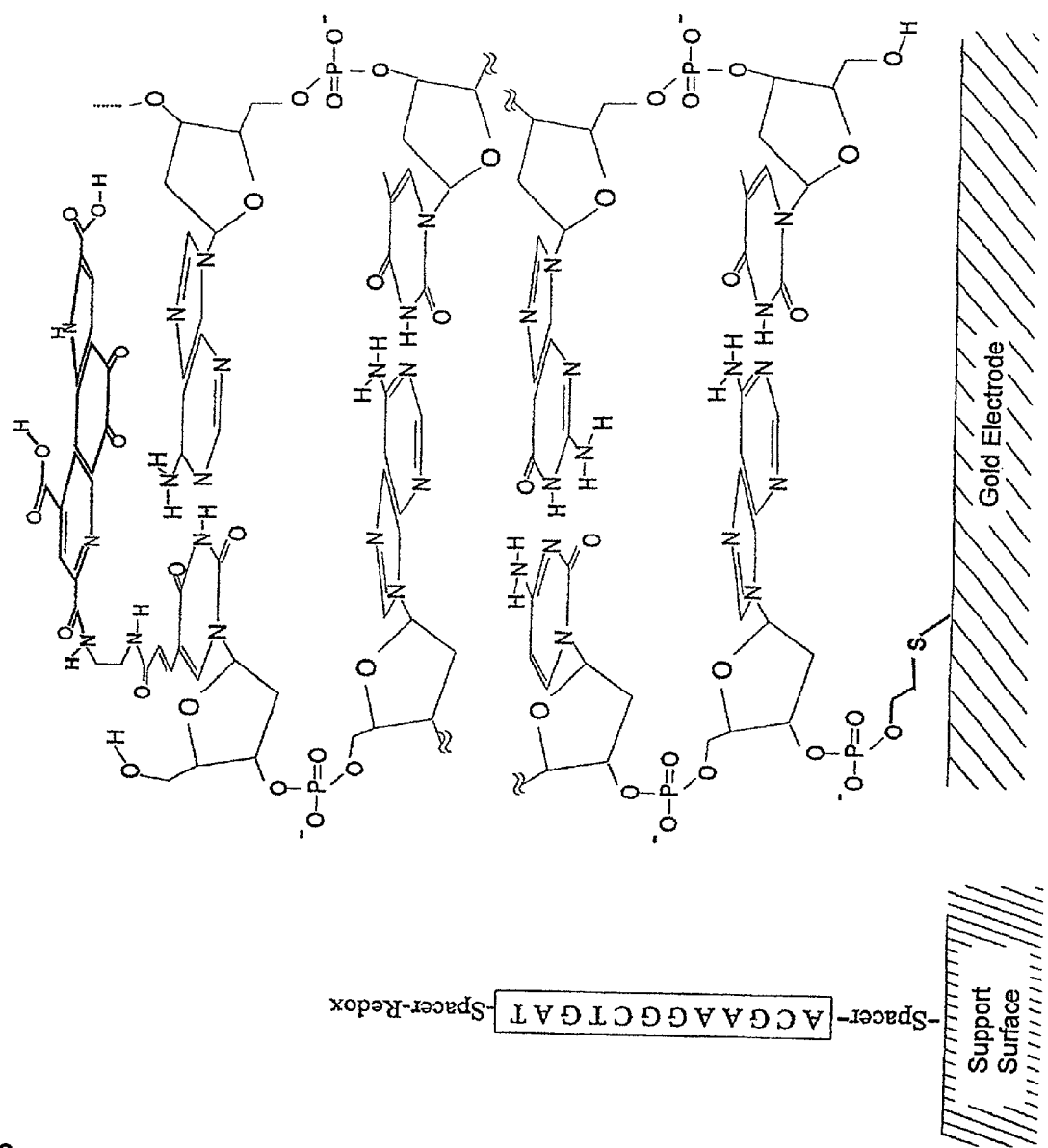
FIG. 3  Shows a schematic illustration of the surface hybrid of the general structure elec-spacer-ss-oligo-spacer-redox with a 12-bp probe oligonucleotide of the exemplary sequence 5'-TAGTCGGAAGCA-3' SEQ ID NO: 1 (left) and Au-S-ss-oligo-PQQ in the hybridized state as an embodiment example of an elec-spacer-ss-oligo-spacer-redox; only a portion of the probe oligonucleotide having a hybridized complementary strand is shown (right), the attachment of the oligonucleotide to the surface redox-active substance PQQ occurred via the spacer —$CH_2$—CH=CH—CO—NH—$CH_2$—$CH_2$—NH—.

An exemplary test site with hybridized target (Au—S-ds-oligo-PQQ) of the general structure elec-spacer-ds-oligo-spacer-redox is shown in FIG. 3. In the example of FIG. 3, the support surface is a gold electrode. The link between the gold electrode and the probe oligonucleotide was formed with the linker (HO—$(CH_2)_2$—S)$_2$, which was esterified with the terminal phosphate group at the 3' end to P—O—$(CH_2)_2$—S—S—$(CH_2)_2$—OH and, following homolytic cleavage of the S—S bond at the gold surface, produced one Au—S bond each, with which 2-hydroxy-mercaptoethanol and mercaptoethanol-bridged oligonucleotide was coadsorbed on the surface. The redox-active substance in the example of FIG. 3 is tricarboxylic pyrrolo-quinoline quinone (PQQ) and one of the three carboxylic acid functions of the PQQ (in the example, the C-7—$CO_2H$ function) was used to covalently attach the PQQ to the probe oligonucleotide (amidation and dehydration with the terminal amino function of the —CH=CH—CO—NH—$CH_2$—$CH_2$—$NH_2$ spacer attached to the C-5 position of the 5' thymine). Both free, unmodified PQQ and PQQ bridged with the support surface via a short spacer of chain length 1–6, such as e.g. —S—$(CH_2)_2$—NH—, or via (modified) double-strand oligonucleotide, e.g. in HEPES buffer with 0.7 molar addition of TEATFB (see abbreviations), is selectively reduced and oxidized in the potential range 0.7 V≧φ≧0.0 V, measured against normal hydrogen electrode.

Figure 4:
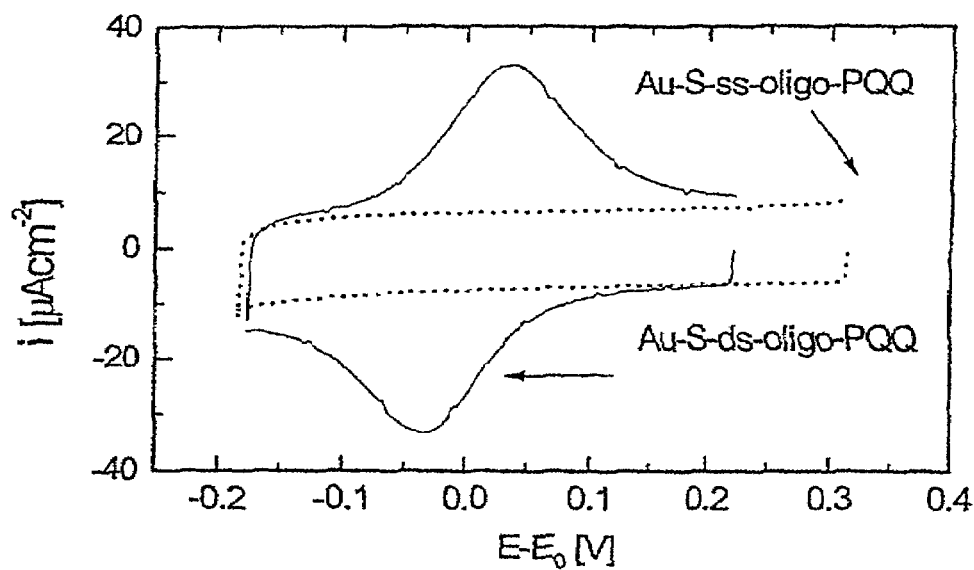
FIG. 4  Shows a cyclic voltammogram of a test site consisting of Au-S-ss-oligo-PQQ (dotted) compared with an identical test site with completely hybridized target (Au-S-ds-oligo-PQQ, solid line)

The electrical communication between the (conductive) support surface and the redox pair bridged via single-strand oligonucleotide in the general structure elec-spacer-ss-oligo-spacer-redox is weak or not present at all. For the exemplary test site Au—S-ss-oligo-PQQ (with 12-bp probe oligonucleotides), this is shown with cyclic voltammetry (FIG. 4). Without wanting to be bound to a theoretical description, it is assumed that the negative charges of the phosphate skeleton cause a mutual repulsion of the oligonucleotide single strands and thus force a formation of the -spacer-ds-oligo-spacer-redox chain (in the direction of the helix axis) at an angle +<70° to the normal of the support support ("standing tubes"). The (hybridized) test site Au—S-ds-oligo-PQQ of FIG. 3 exhibits a formation having φ=30°. Due to the length of the -spacer-ds-oligo-spacer-redox chain (e.g. approx. 40 Å length of a 12-base-pair oligonucleotide; the spacers and the attached PQQ are about 10 Å long), if φ<70°, a distance of >17 Å results between the surface support and the redox-active substance. As a result, the possibility of a direct electron or hole transfer between the support and the redox-active substance can be excluded. By treating the test site(s) with an oligonucleotide solution to be examined, in the case of hybridization between probe and target, there will be increased conductivity between the support surface and the redox pair bridged via a double-strand oligonucleotide. The change in the conductivity manifests itself cyclic voltammetrically in a significant current flow between the support surface and the redox-active substance (FIG. 4). It is thus possible to detect the sequence-specific hybridization of the target with the probe oligonucleotides using electrochemical methods such as e.g. cyclic voltammetry.

Figure 5:
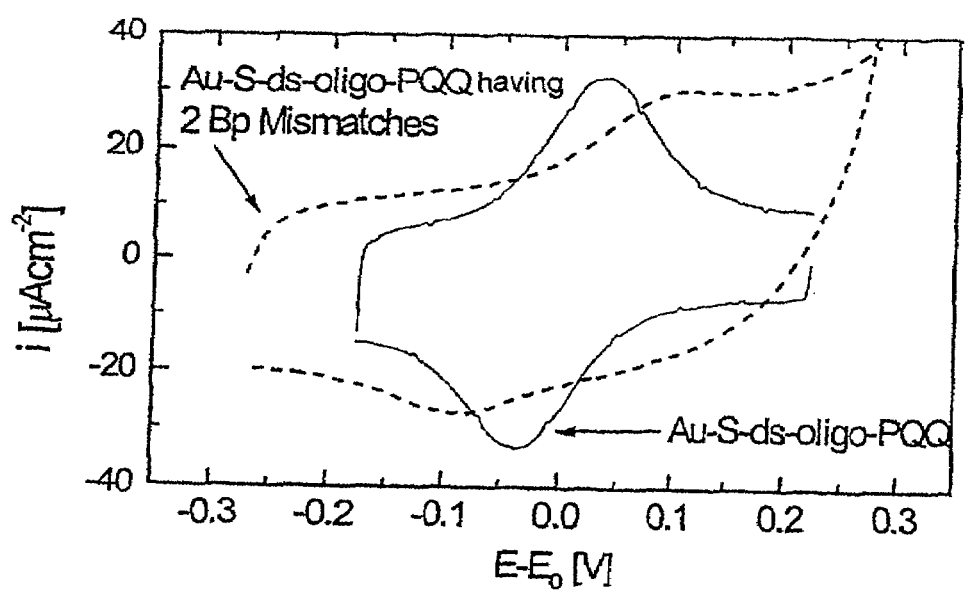
FIG. 5  Shows a cyclic voltammogram of a test site with completely hybridized target (Au-S-ds-oligo-PQQ) (solid line) compared with a test site with hybridized target that exhibits 2 base-pair mismatches (Au-S-ds-oligo-PQQ with 2 bp mismatches, broken)

In addition, defective base pairings (base-pair mismatches) can be recognized by means of a modified cyclic voltammetric characteristic (FIG. 5). A mismatch manifests itself in a greater potential difference between the current maximums of electroreduction and electroreoxidation (reversal of electroreduction when potential feed direction is reversed), or electrooxidation and electroreduction in a cyclic voltammetrically reversible electron transfer process between the electrically conducting support surface and the redox-active substance. This fact has an advantageous effect primarily on amperometric detection because there, the current can be tested at a potential at which the perfectly hybridizing oligonucleotide target supplies significant current, but the defectively paired oligonucleotide target does not. In the example of FIG. 5, this is possible at a potential $E–E_0$ of approx. 0.03 V.

EXAMPLE 1

Producing the Au—S-ds-oligo-PQQ oligonucleotide electrode. The production of Au—S-ds-oligo-PQQ is divided into 4 subsections, namely producing the support surface, hybridizing the probe oligonucleotide with the complementary double strand (hybridization step), derivatizing the support surface with the double-strand oligonucleotide (incubation step) and attaching the redox-active substance (redox step).

An approx. 100 nm thin gold film on mica (muscovite platelets) forms the support for the covalent attachment of the double-strand oligonucleotides. To this end, freshly cleaved mica was purified with an argon-ion plasma in an electrical discharge chamber and gold (99.99%) was applied, by means of electrical discharge, in a layer thickness of approx. 100 nm. Thereafter, the gold film was freed of surface impurities (oxidation of organic accumulations) with 30% $H_2O_2$, /70% $H_2SO_4$ and immersed in ethanol for approx. 20 minutes to dispel any oxygen adsorbed to the surface. After rinsing the support surface with bidistilled water, a previously prepared $1\times10^4$ molar solution of the (modified) double-strand oligonucleotide is applied to the horizontally disposed surface, such that the entire support surface is moistened (incubation step, see also below).

To prepare the ds oligonucleotide solution, a double-modified 12-bp single-strand oligonucleotide of the sequence 5'-TAGTCGGAAGCA-3' SEQ ID NO: 1 was used, which is esterified with (HO—$(CH_2)_2$—$S)_2$ at the phosphate group of the 3' end to P—O—$(CH_2)_2$—S—S—$(CH_2)_2$—OH. At the 5' end, the terminal base of the oligonucleotide, thymine, is modified at the C-5 carbon with —CH=CH—CO—NH—$CH_2$—$CH_2$—$NH_2$. A $2\times10^4$ molar solution of this oligonucleotide in the hybridization buffer (10 mM Tris, 1 mM EDTA, pH 7.5 with 0.7 molar addition of TEATFB, see abbreviations) was hybridized with a $2\times10^{-4}$ molar solution of the (unmodified) complementary strand in the hybridization buffer at room temperature for approx. 2 hours (hybridization step). During a reaction time of approx. 12–24 h, the disulfide spacer P—O—$(CH_2)_2$—S—S—$(CH_2)_2$—OH of the oligonucleotide was homolytically cleaved. In this process, the spacer forms a covalent Au—S bond with the Au atoms of the surface, thus causing to a 1:1 coadsorption of the ds-oligonucleotide and the 2-hydroxy-mercaptoethanol.

The gold electrode modified in this way with a dense (1:1) monolayer consisting of ds-oligonucleotide and 2-hydroxy-mercaptoethanol was washed with bidistilled water and subsequently moistened with a solution of $3\times10^3$ molar quinone PQQ, 102 molar EDC, and $10^{-2}$ molar sulfo-NHS in HEPES buffer. After a reaction time of approx. 1 h, the —CH=CH—CO—NH—$CH_2$—$CH_2$—$NH_2$ spacer covalently attaches the PQQ (amidation between the amino group of the spacer and an acid function of the PQQ, redox step).

Resolution of the surface composition with XPS (X-Ray Photoelectron Spectroscopy) showed a maximally densely packed monolayer of 1:1 coadsorbed ds-oligonucleotide and 2-hydroxy-mercaptoethanol ($4.7\times10^{12}$ ds-oligonucleotide/$cm^2$), the long axis (direction of the helix axis) of the ds-oligonucleotides forming an angle of φ≈ 300 with the surface normal of the gold surface.

EXAMPLE 2

Producing the Au—S-ss-oligo-PQQ oligonucleotide electrode. Analogously to the production of the Au—S-ds-oligo- PQQ system, the support surface is derivatized with modified single-strand oligonucleotide, dispensing with only the hybridization of the modified oligonucleotide of the sequence 5'-TAGTCGGAAGCA-3' SEQ ID NO: 1 with its complementary strand and, in the incubation step, using only the double-modified 12 bp single-strand probe oligonucleotide (see Example 1) in the form of a 1×10$^{-4}$ molar solution in water and in the presence of 10$^{-2}$ molar Tris, 10$^{-3}$ molar EDTA and 0.7 molar TEATFB (or 1 molar NaCl) at pH 7.5. The redox step was carried out as indicated in Example 1.

EXAMPLE 3

Producing the Au—S-ds-oligo-PQQ oligonucleotide electrode having 2 bp mismatches. The production of a support surface derivatized with modified double-strand oligonucleotide was carried out analogously to the production of the Au—S-ds-oligo-PQQ system, but only in hybridizing the modified oligonucleotide of the sequence 5'-TAGTCGGAAGCA-3' SEQ ID NO: 1 was a complementary strand used (sequence: 5'-ATCAGATTTCGT-3') SEQ ID NO: 2, in which bases no. 6 and 7 (counted from the 5' end), which are actually complementary, were modified from C to A or from C to T to introduce two base-pair mismatches.

EXAMPLE 4

Producing an Au—S-ss-oligo-PQQ oligonucleotide electrode having greater inter-oligonucleotide distance. In producing the test sites, care must be taken that, in derivatizing the support surface with single-strand probe oligonucleotide, sufficient space remains between the attached single-strands to allow a hybridization with the target oligonucleotide. To this end, three different methods of proceeding present themselves: (a) Producing an Au—S-ds-oligo-PQQ electrode as described in Example 1, with subsequent thermal dehybridization of the double strands at temperatures of T>40° C. (b) Producing an Au-ss-oligo-PQQ electrode as described in Example 2, but in the incubation step for derivatizing the gold surface with (double-derivatized) single-strand oligonucleotide, 10$^{-5}$ to 10$^{-1}$ molar 2-hydroxy-mercaptoethanol or another thiol or disulfide linker of suitable chain length is added (depending on the desired inter-oligonucleotide distance) and coadsorbed on the gold surface together with the single-strand oligonucleotide. (c) Producing an Au-ss-oligo-PQQ electrode as described in Example 2, but omitting the 0.7 molar addition of electrolytes (TEATFB in the Example) in the incubation step for derivatizing the gold surface with (double-derivatized) single-strand oligonucleotide. Due to the absence of the salt, the phosphate groups and nitrogen-base atoms of the oligonucleotide are not electrostatically shielded and interact strongly with the gold surface. Because of this, a shallow accumulation of the oligonucleotides results on the electrode surface ($\phi$>600) and significantly fewer oligonucleotides are bound per surface unit. Thereafter, the oligonucleotides may be returned to the desired position by covalently attaching in a second incubation step (before or after attaching the PQQ) a 2-hydroxy-mercaptoethanol or another thiol or disulfide linker of suitable chain length to the surface gold atoms that are still free. To do this, the electrode that is less densely covered with single-strand oligonucleotide is moistened, before or after modification with PQQ (Au—S-ss-oligo or Au—S-ss-oligo-PQQ), with an approx. 5×10$^{-2}$ molar solution of 2-hydroxy-mercaptoethanol or another thiol or disulfide linker of suitable chain length in ethanol or HEPES buffer (or a mixture thereof, depending on the solubility of the thiol), and incubated for 2–24 h.

EXAMPLE 5

Carrying out the cyclic voltammetry measurements. The cyclic voltammetry measurements were made using a computer-controlled bipotentiostat (CH Instruments, Model 832) at room temperature in a standard cell having a 3-electrode configuration. The modified gold electrode was used as the working electrode, a platinum wire served as the auxiliary electrode (counter electrode), and an Ag/AgCl electrode with internal saturated KCl solution, separated from the probe space via a Luggin capillary, was used as the reference electrode to determine the potential. Serving as an electrolyte was 0.7 molar TEATFB or 1 molar NaCl. A cyclic voltammogram of the Au—S-ds-oligo-PQQ electrode is shown in FIG. 4 in comparison with an Au—S-ss-oligo-PQQ electrode, and the effect of the 2 bp mismatches on the cyclic voltammogram of the Au—S-ds-oligo-PQQ electrode is shown in FIG. 5. The potentials are each indicated as E-Eo, i.e. relative to the half-wave potential.

In FIG. 4, shows clearly a significantly greater current flow as compared with the non-hybridized form is clearly evident when a double-strand oligonucleotide is present. This allows sequence-specific hybridization events to be detected. From FIG. 5 it becomes clear that, in the case of hybridization with a target oligonucleotide strand that exhibits 2 base-pair mismatches, for one thing, a weaker current flows, and for another, the difference of the current maximums is increased.

The invention claimed is:

1. A method of producing a modified conductive surface, wherein a nucleic acid oligomer or a nucleic acid oligomer modified by attaching a redox-active substance that is selectively oxidizable and reducible at a potential $\phi$ with $2.0 \text{ V} \geq \phi \leq -2.0 \text{ V}$, measured against a normal hydrogen electrode, is hybridized with the nucleic acid oligomer strand which is complementary to the nucleic acid oligomer or the modified nucleic acid oligomer and applied to a conductive surface and is in the form of the double-strand hybrid; and
    one or more kinds of nucleic acid oligomers in the form of the double-strand hybrid are bound to a conductive surface and only the nucleic acid oligomers bound to the conductive surface are modified by attaching a redox-active substance to the nucleic acid oligomers.

2. A method of producing a modified conductive surface, wherein a nucleic acid oligomer or a nucleic acid oligomer modified by attaching a redox-active substance that is selectively oxidizable and reducible at a potential $\phi$ with $2.0 \text{ V} \geq \phi \geq -2.0 \text{ V}$, measured against a normal hydrogen electrode, is hybridized with the nucleic acid oligomer strand which Is complementary to the nucleic acid oligomer or the modified nucleic acid oligomer and applied to a conductive surface and is in the form of the double-strand hybrid, which is thermally dehybridized following application to the conductive surface.

3. The method according to claim 2, wherein the double-strand hybrid is applied to the conductive surface in the presence of further chemical compounds also attached to the conductive surface.

4. The method according to claim 2, wherein the nucleic acid oligomers or the modified nucleic acid oligomers are attached to the conductive surface covalently or by means of physisorption.

5. The method according to claim 2, wherein the nucleic acid oligomers or the modified nucleic add oligomers are covalently attached to branched or linear molecular moieties of any composition and chain length and these molecular moieties are attached to the conductive surface covalently or by mean so physisorption.

6. The method according to claim 2, wherein one or more kinds of nucleic acid oligomers in the form of the double-strand hybrid are bound to a conductive surface and only the nucleic acid oligomers bound to the conductive surface are modified by attaching a redox-active substance to the nucleic acid oligomers.

* * * * *